United States Patent
Buge et al.

(10) Patent No.: US 10,821,076 B2
(45) Date of Patent: *Nov. 3, 2020

(54) SELF-FOAMING CLEANSING COMPOSITION CONTAINING CLOBETASOL PROPIONATE, AND USE THEREOF IN THE TREATMENT OF PSORIASIS

(71) Applicant: GALDERMA RESEARCH & DEVELOPMENT, Biot (FR)

(72) Inventors: Jean-Christophe Buge, Nice (FR); Karine Nadau-Fourcade, Villeneuve Loubet (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 1 day.

This patent is subject to a terminal disclaimer.

(21) Appl. No.: 15/764,242

(22) PCT Filed: Sep. 27, 2016

(86) PCT No.: PCT/EP2016/073011
§ 371 (c)(1),
(2) Date: Jun. 11, 2018

(87) PCT Pub. No.: WO2017/055294
PCT Pub. Date: Apr. 6, 2017

(65) Prior Publication Data
US 2018/0280299 A1    Oct. 4, 2018

(30) Foreign Application Priority Data
Sep. 29, 2015   (FR) .................................. 15 59207

(51) Int. Cl.
| | | |
|---|---|---|
| *A61K 9/12* | (2006.01) | |
| *A61K 9/00* | (2006.01) | |
| *A61K 31/573* | (2006.01) | |
| *A61P 17/06* | (2006.01) | |
| *A61K 8/04* | (2006.01) | |
| *A61K 8/24* | (2006.01) | |
| *A61K 8/365* | (2006.01) | |
| *A61K 8/63* | (2006.01) | |
| *A61K 47/02* | (2006.01) | |
| *A61K 47/12* | (2006.01) | |
| *A61Q 19/00* | (2006.01) | |

(52) U.S. Cl.
CPC .............. *A61K 9/122* (2013.01); *A61K 8/046* (2013.01); *A61K 8/24* (2013.01); *A61K 8/365* (2013.01); *A61K 8/63* (2013.01); *A61K 9/007* (2013.01); *A61K 9/0014* (2013.01); *A61K 31/573* (2013.01); *A61K 47/02* (2013.01); *A61K 47/12* (2013.01); *A61P 17/06* (2018.01); *A61Q 19/00* (2013.01); *A61K 2800/22* (2013.01); *A61K 2800/88* (2013.01)

(58) Field of Classification Search
CPC ........ A61K 8/63; A61K 9/122; A61K 9/0014; A61K 8/24; A61K 9/007; A61K 8/365; A61K 31/573; A61K 47/12; A61K 8/046; A61K 47/02; A61K 2800/22; A61K 2800/88; A61P 17/06; A61Q 19/00
See application file for complete search history.

(56) References Cited

U.S. PATENT DOCUMENTS

| | | |
|---|---|---|
| 5,952,372 A | 9/1999 | McDaniel |
| 6,133,310 A | 10/2000 | Parks |
| 6,177,092 B1 * | 1/2001 | Lentini ................. A61K 8/046 424/401 |
| 6,649,186 B1 | 11/2003 | Robinson et al. |
| 2002/0061855 A1 | 5/2002 | Parks |
| 2004/0184992 A1 | 9/2004 | Abram |
| 2005/0123487 A1 | 6/2005 | Spadini et al. |
| 2007/0237724 A1 | 10/2007 | Abram et al. |
| 2009/0191248 A1 | 7/2009 | Hoffman et al. |
| 2009/0214628 A1 | 8/2009 | De Rijk et al. |

(Continued)

FOREIGN PATENT DOCUMENTS

| | | |
|---|---|---|
| CN | 104382863 A | 3/2015 |
| DE | 10 2008 029 357 A1 | 12/2009 |

(Continued)

OTHER PUBLICATIONS

International Search Report and English translation dated Nov. 25, 2016 corresponding to International Patent Application No. PCT/EP2016/073011, 9 pages.

(Continued)

*Primary Examiner* — Lezah Roberts
(74) *Attorney, Agent, or Firm* — Foley & Lardner LLP; Sunit Talapatra

(57) ABSTRACT

A self-foaming composition for a topical application is described. The composition can include a medium which is cosmetically- or pharmaceutically-compatible with a topical application, and clobetasol propionate. The composition can include a small quantity of foaming surfactants. The composition includes: at least one intermediate composition B including a gas-generating agent; at least one intermediate composition A including an agent for activating the gas-generating agent; and clobetasol propionate being present in at least one of the intermediate compositions A and B. Also described, is a kit or a single container including a plurality of compartments including such a composition.

36 Claims, No Drawings

(56) References Cited

U.S. PATENT DOCUMENTS

| | | | |
|---|---|---|---|
| 2010/0291160 A1* | 11/2010 | Carver | A61K 9/0014 424/400 |
| 2011/0008267 A1 | 1/2011 | Arkin et al. | |
| 2011/0236503 A1 | 9/2011 | Kalli | |
| 2012/0114574 A1 | 5/2012 | Touitou | |
| 2013/0244976 A1 | 9/2013 | Inamoto et al. | |
| 2013/0317108 A1 | 11/2013 | At | |
| 2013/0338230 A1 | 12/2013 | At | |
| 2013/0338235 A1 | 12/2013 | At | |
| 2014/0364504 A1 | 12/2014 | Uddin | |
| 2015/0306124 A1 | 10/2015 | Manetta et al. | |
| 2017/0172877 A1 | 6/2017 | Buge et al. | |
| 2017/0172972 A1 | 6/2017 | Buge et al. | |

FOREIGN PATENT DOCUMENTS

| | | |
|---|---|---|
| EP | 1 043 023 A1 | 10/2000 |
| FR | 2761600 A1 | 10/1998 |
| FR | 2924944 A1 | 6/2009 |
| FR | 2943914 A1 | 10/2010 |
| JP | 2002-529391 A | 9/2002 |
| JP | 2004-217675 A | 8/2004 |
| WO | WO-00/27356 A1 | 5/2000 |
| WO | WO-03/030664 A1 | 4/2003 |
| WO | WO-2004/037225 A2 | 5/2004 |
| WO | WO-2005/058272 A1 | 6/2005 |
| WO | WO-2009/069006 A2 | 6/2009 |
| WO | WO-2012/001065 A2 | 1/2012 |
| WO | WO-2012/085480 A1 | 6/2012 |
| WO | WO-2012/085481 A1 | 6/2012 |
| WO | WO-2012/085483 A1 | 6/2012 |
| WO | 2014/201541 A1 | 12/2014 |
| WO | WO-2015/082659 A1 | 6/2015 |

OTHER PUBLICATIONS

Written Opinion of the International Searching Authority dated Nov. 25, 2016 corresponding to International Patent Application No. PCT/EP2016/073011, 6 pages.

Onset Therapeutics, LLC, "Benzefoam Ultra", Drug Information Online—Drugs.com, Apr. 3, 2011, XP002739766. 9 pages.

Wikimedia Commons; "Citric Acid Speciation" https://commons.wikimedia.org/wiki/File:Citric_acid_speciation.png; accessed Jan. 10, 2020 (Year: 2011).

* cited by examiner

SELF-FOAMING CLEANSING COMPOSITION CONTAINING CLOBETASOL PROPIONATE, AND USE THEREOF IN THE TREATMENT OF PSORIASIS

CROSS-REFERENCE TO PRIOR APPLICATIONS

This application is a National Stage of PCT/EP2016/073011, filed Sep. 27, 2016, and designating the United States (published on Apr. 6, 2017, as WO 2017/055294 A1), which claims priority under 35 U.S.C. § 119 to French Application No. 1559207, filed Sep. 29, 2015, each hereby expressly incorporated by reference in its entirety and each assigned to the assignee hereof.

The present invention relates to a rinse-off cleansing topical product in the form of a foam for the pharmaceutical or cosmetic treatment of the skin, effective especially for the treatment of psoriasis of the scalp, and containing clobetasol propionate.

Psoriasis is one of the commonest skin diseases among all the chronic skin diseases. The scalp is one of the sites susceptible to psoriasis; it essentially causes erythema, desquamation, hyperkeratosis or pruritus and may also be responsible for a reduction in the hair density. The treatments used to date contain salicylic acid, local steroids or tar. These treatments are unpleasant, especially the application of tar, and require long applications, especially when hair salves are used.

For the purpose of improving the quality of life of the patient, without, however, reducing the therapeutic effect of the treatment, foaming compositions containing corticosteroids have been developed. More particularly, the application time of these foaming compositions is reduced relative to the standard treatment.

Clobetasol propionate is a class 1 dermocorticoid, namely a corticoid with very strong activity. Like other cortisone derivatives for local use, it impedes the renewal and multiplication of skin cells. Its efficacy on psoriasis, and particularly psoriasis of the scalp, is proven.

There is a need for novel galenical forms of foaming cleansing product in which clobetasol propionate is stable, well tolerated, efficient and pleasant to apply.

Despite the new generations of foaming surfactants, hygiene products and most particularly cleansing products remain irritant and may lead to mediocre tolerance of the product.

However, the user associates the volume and the amount of foam with the cleansing power and the efficacy thereof. There is thus a need to develop novel foaming galenical forms containing little or no foaming surfactants, which are efficient and at the same time meet the user's expectations, while at the same time improving the tolerance of this type of product.

Specifically, in general, foaming compositions contain a large amount of foaming surfactants. This high content gives rise to skin irritation. The present invention aims at proposing a composition that is particularly well tolerated, as shown by the examples illustrating one of the methods for evaluating the tolerance presented hereinbelow.

Various methods exist for evaluating the tolerance of a pharmaceutical or cosmetic product for cutaneous use, among which may be mentioned the in vivo "in used" or "human patch test" test, but also the in vitro test, such as the test for measurement of the irritation on Reconstructed Human Epidermis (RHE) described in the OECD TG 439 protocol. The latter method is described in detail in example 3.

Cleansing foams or foaming compositions currently exist on the market. However, they all have a certain number of drawbacks.

This is because four types of cleansing foams or foaming compositions exist:

Aerosols, in which the foam is generated by a propellant gas but with the drawback of being aerosols having the well-known risks of the latter (contamination and breathing risks in particular).

Formulations rich in foaming surfactants. These formulations have the drawback of being slightly irritant in the best of cases; they are usually irritant. Furthermore, active agents that are sensitive to the presence of foaming surfactants in relatively large amount cannot be envisaged in this type of composition.

Rinseable expanded creams in which air bubbles are introduced into the product by means of a particular manufacturing process. This manufacturing process has the drawback of being industrially very restricting and requires heavy investment in the industrial packaging equipment.

Foaming formulations that are sparingly rich in foaming surfactants but packaged in a packaging/wrapping equipped with a foam-generating mechanical system (pump with a grate of Pulvorex type). This type of packaging has the drawback of being compatible only with very fluid galenical forms.

Thus, there is still a need to develop a pharmaceutical composition whose galenical form is different from the known galenical forms so as to overcome the drawbacks thereof and thus to allow the use of clobetasol propionate in dissolved form in well-tolerated rinseable cleansing foaming compositions intended for topical application in humans.

The aim of the present invention is thus to propose such a composition that meets these needs.

The Applicant has thus developed a novel cosmetic and/or pharmaceutical composition, intended for rinse-off topical application, which is in the form of a self-foaming composition (preferably a self-foaming shampoo) with little foaming surfactant, i.e. with a content of foaming surfactant that is advantageously less than or equal to 2.5% by weight of active material relative to the weight of the total composition.

The term "foaming surfactant" means surfactants which produce a voluminous, stable and creamy foam when they are mixed with water according to tests that are well known to those skilled in the art.

The following constitute foaming surfactants in particular: anionic surfactants, cationic surfactants, amphoteric surfactants and nonionic surfactants of the family of alkylpolyglucosides and glucamides.

The galenical form according to the invention has the advantage of ensuring good stability of clobetasol propionate. Furthermore, this formulation advantageously results in the production of a mild foam which is fully tolerated and non-irritant, which allows treatment and cleansing of the scalp while overcoming the problems of tolerance and satisfying the customer in terms of the quality of the foam.

Finally, advantageously, this galenical form does not require, for the implementation thereof, the use of propellant gases or aerosols. Thus, "aerosol" or "spray" foams are excluded from the scope of the invention. Likewise, the rinsable foaming compositions of the prior art of standard foaming composition type rich in foaming surfactants and/or the foaming formulations with a reduced content of surfactants but requiring a mechanical foam-generating system (Pulvorex type) are also excluded from the invention. This is likewise the case for foaming compositions involving an expanding process.

Finally, a subject of the present invention is the cosmetic use of the composition according to the invention, by topical application of the latter to the skin or the scalp, and also a medicament intended for topical application to the skin and the scalp, comprising such a composition. According to the invention, after its application, the composition is removed by rinsing.

A subject of the present invention is also the composition according to the invention, for its use in the treatment of psoriasis.

The present invention will be described in greater detail in the description and the examples hereinbelow. In the description that follows, unless expressly indicated, the contents of the ingredients are expressed in terms of amount of active material.

This composition is capable of taking the form of a foam solely by virtue of its composition, and may thus also be defined as a self-foaming composition for topical application.

A first subject of the present invention is consequently a composition containing clobetasol propionate, intended for topical application, which is provided in the form of a foam, advantageously of semisolid consistency, which preferably does not contain much foaming surfactant (a content of less than or equal to 2.5% by weight relative to the weight of the total composition), and which comprises a medium that is cosmetically or pharmaceutically compatible with rinse-off topical application, in particular to the skin and the scalp.

The term "composition in the form of a foam" (also referred to hereinbelow as a self-foaming composition) means a composition of semisolid consistency having an aerated form comparable to a foam.

Preferentially, the gas-generating agent is present in one of the intermediate formulations mentioned previously.

The self-foaming composition according to the present invention comprises two intermediate compositions or formulations in variable proportions and in particular the ingredients below:
at least one intermediate composition or formulation A comprising an agent for activating the gas-generating agent mentioned below,
at least one intermediate composition or formulation B comprising a gas-generating agent,
clobetasol propionate contained in at least one of said intermediate formulations A and B.

Preferably, the clobetasol propionate is contained in intermediate composition A.

The composition according to the invention is self-foaming, i.e. it foams by simple mixing of the intermediate compositions A and B. A subject of the present invention is also the composition in foam form resulting from the mixing of said intermediate compositions A and B.

Depending on the agents present in the intermediate composition (or intermediate formulation), and also on the proportions thereof in said composition, this composition may be in any galenical form or may have any known texture that may be used in cosmetics and/or in pharmaceuticals for topical application.

Preferably, each intermediate composition (or intermediate formulation) according to the invention may thus be, for example, in the form of gel, emulsion (cream, surfactant-free cream, lotion, milk or fluid cream), serum, solution or suspension, and preferentially in the form of emulsion (cream, surfactant-free cream, lotion, milk or fluid cream) or gel. All of these formulations are included in the context of the invention.

According to the invention, each intermediate composition (or formulation) may have a viscosity (measured at 25° C. and at atmospheric pressure) of between 1 cP and 500 000 cP, advantageously between 500 cP and 350 000 cP, measured with a conventional method of Brookfield RV DV-II type: spindle 6, speed 2.

According to the invention, the term "agent for activating the gas-generating agent" means an ingredient which, by chemical reaction with the gas-generating agent, releases a gas. Preferentially, an acid/base reaction is involved.

According to the invention, the gas generated by the gas-generating agent may be any physiologically compatible gas which allows the production of a foam, for instance carbon dioxide ($CO_2$) or oxygen ($O_2$). Preferably, the gas generated from the gas-generating agent is carbon dioxide ($CO_2$).

According to the invention, since the gas concentration may vary, the amount of bubbles in the composition may vary and may thus give a composition which may range from not very aerated to very strongly aerated.

Thus, according to the invention, the self-foaming composition may preferentially be in any form ranging from aerated to a highly expanded foam.

The composition according to the invention is suitable for topical application and may also comprise a physiologically acceptable medium, i.e. a medium that is compatible with the skin and integuments. It is preferably a cosmetically or pharmaceutically acceptable medium.

In addition, the composition may comprise any active agent that may have activity, optionally therapeutic activity. These active agents may be chosen, inter alia, from emollients, humectants, free-radical scavengers, anti-inflammatory agents, vitamins, depigmenting agents, antiacne agents, antiseborrheic agents, antifungal agents, keratolytic agents, sunscreens, slimming agents and skin-coloring agents.

According to the invention, the composition in foam form (i.e. ready to be applied) has a pH of between 2 and 8, preferentially between 3 and 7.

Insofar as the intermediate composition(s) (or formulation(s)) require storage in at least two compartments for reasons of stability of the ingredients, the present invention relates either to a single compartmentalized container (each compartment receiving one intermediate formulation) and preferably comprising two or three compartments, or to a kit comprising each intermediate formulation stored independently from each other and physically separated.

Intimate extemporaneous mixing (directly on the skin or on any other support) of the intermediate formulations makes it possible to obtain the composition in foam form according to the invention.

More specifically, the intermediate composition (or formulation) A may be in the form of a solution, an emulsion (lotion, cream, emulsifier-free cream, milk or fluid cream) or a gel. This composition advantageously contains the agent for activating the gas-generating agent, preferentially an acid, in a sufficient amount (which may be in the form of an acid/base buffer at acidic pH), which may be, as a nonlimiting example, the citric acid/sodium citrate pair.

Formulation B may be in the form of a solution, a gel or an emulsion (lotion, cream, emulsifier-free cream, milk or fluid cream). This composition advantageously contains, in a sufficient amount, a gas-generating agent which may in particular be sodium bicarbonate.

Thus, a subject of the invention is also a kit or a single multi-compartment container as defined previously, for the extemporaneous preparation of a composition in foam form according to the invention, separately comprising at least two intermediate formulations (or intermediate compositions):
- an intermediate formulation A comprising at least one agent for activating the gas-generating agent; and
- an intermediate formulation B comprising at least one gas-generating agent;
- clobetasol propionate being contained in at least one of said intermediate formulations A and B.

Preferably, the clobetasol propionate is contained in intermediate composition A.

Gas-Activating Agent:

The agent for activating the gas-generating agent (also referred to as the "gas-activating agent") is a compound which reacts with the gas-generating agent via a chemical reaction (preferably an acid/base reaction) which releases a gas.

It is advantageously an acid, a partially salified polyacid salt or a buffer solution of a weak acid and of its conjugate base, or a mixture of such compounds.

According to the invention, the acid/base buffer of said acid may be any acid/base buffer of the weak acid, for instance a citric acid/sodium citrate buffer or a tartaric acid/sodium tartrate buffer. Mention will preferably be made of α-hydroxy acids, which are weak acids preferentially with a pKa of between 2 and 6, such as citric acid, tartaric acid, malic acid or lactic acid, but also phosphoric acid and pyrophosphoric acid and optionally the partially salified salts thereof, such as disodium pyrophosphate or sodium dihydrogen phosphate, also known as monosodium phosphate.

Preferentially, according to the invention, the gas-activating agent is chosen from a tartaric acid/tartrate salt (for example sodium tartrate) buffer; a citric acid/sodium citrate buffer alone; phosphoric acid, sodium phosphate, disodium pyrophosphate, which are alone or as a mixture with the citric acid/sodium citrate buffer.

According to a very preferred embodiment, the gas-activating agent is a citric acid/sodium citrate buffer, alone or as a mixture with sodium phosphate and/or disodium pyrophosphate.

In compositions for sensitive skin or for damaged skin, such as skin affected by psoriasis, the content of citric acid/sodium citrate is preferably less than or equal to 2.4%, relative to the total weight of the intermediate composition A, so as to limit any risk of stinging. In order to improve the tolerance and to avoid the sensation of stinging, preferably, the citric acid/sodium citrate buffer is used as a mixture with disodium pyrophosphate or sodium dihydrogen phosphate.

According to the invention, said gas-activating agent may be present in the intermediate formulation A in an amount that may range from 0.001% to 95% by weight relative to the total weight of the intermediate composition A.

Gas-Generating Agent:

The term "gas-generating agent" means any agent which has the property of generating a gas via a chemical reaction. Mention will be made in this regard of any compound which, when it is mixed with a weak acid, can form a gas via a chemical reaction equivalent to the following:

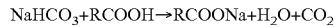

$$NaHCO_3 + RCOOH \rightarrow RCOONa + H_2O + CO_2$$

According to the invention, the gas generated from the gas-generating agent present in the intermediate composition B is preferably carbon dioxide ($CO_2$).

According to the invention, the gas-generating agent is preferably chosen from sodium bicarbonate, potassium bicarbonate, sodium carbonate and potassium carbonate, and mixtures thereof.

Preferentially, according to the invention, the intermediate formulation B comprises an agent which generates carbon dioxide, this agent particularly preferably being sodium bicarbonate.

Said gas-generating agent may be present in the intermediate formulation B in an amount ranging from 1% to 10% by weight and preferentially from 2% to 8% by weight, relative to the weight of the intermediate composition B.

According to the invention, the intermediate formulation A may have an acidic pH, advantageously of between 1 and 6, and the intermediate formulation B may have a basic pH, advantageously of between 7 and 12.

According to the invention, one or both of the intermediate formulations comprise clobetasol propionate in an amount ranging from 0.0001% to 1% by weight, preferentially from 0.001% to 0.5% by weight, and more preferentially from 0.03% to 0.2% by weight, relative to the weight of the total composition.

In the present description, the term "total composition" or "total formulation" means the composition of the product in foam form after said intermediate compositions have been mixed.

Preferably, clobetasol propionate is contained in composition A formulated at acidic pH so as to optimize its stability.

The intermediate formulation A may be in any galenical form that is compatible with the galenical form desired for the final composition obtained by mixing formulation A with formulation B. Advantageously, formulation A may be a gel, a solution, a suspension or an emulsion (cream, surfactant-free cream, lotion, milk or fluid cream), preferably a gel ensuring the stability of the clobetasol propionate. According to a particularly preferred embodiment, the intermediate formulation A is in gel form.

The intermediate formulation B may be in any galenical form that is compatible with the galenical form desired for the final composition obtained by mixing formulation B with formulation A. Advantageously, formulation B may be a gel, a solution, a suspension or an emulsion (cream, surfactant-free cream, lotion, milk or fluid cream), preferably a gel, or a solution.

According to one embodiment of the invention, one of the two intermediate formulations (i.e. intermediate formulation A or intermediate formulation B) is in the form of a gel. In this embodiment, the other intermediate formulation is preferably not in gel form.

Each formulation of the kit or of the multi-compartment container as defined previously in accordance with the invention comprises a physiologically acceptable medium which conveys the compound(s) and which is chosen such that the compounds are capable of reacting with each other to form a self-foaming composition during the mixing of at least the intermediate formulations A and B.

Thus, the extemporaneous mixing of at least two formulations, for example formulation A and formulation B, creates the composition in foam form according to the invention.

During the mixing of the two formulations A and B, the gas-generating agent, such as sodium bicarbonate, may react with the gas-activating agent, such as the acid, and thus give in particular the salt corresponding to the acid, water and $CO_2$ gas. It is this gas, trapped in the bubbles of the composition, which creates the foam which characterizes the self-foaming composition of the invention.

Thus, by mixing at least intermediate formulation A and intermediate formulation B, the foam composition, referred to as the total composition, according to the invention is obtained. Unreacted gas-activating agent and/or gas-generating agent may, of course, remain in the composition obtained after mixing at least formulations A and B.

Advantageously, the kit or the single multi-compartment container according to the invention may be designed so that, during the preparation of the composition according to the invention, the intermediate formulations A and B can be mixed in an A/B weight ratio ranging from 0.5 to 2, preferentially from 0.5 to 1.5, more preferentially close to 1 (i.e. from 0.9 to 1.1) and even more preferentially 1. This means that the kit can be designed to simultaneously release doses (by weight) of the intermediate compositions A and B that may be in a weight ratio ranging from 2 doses of B per 1 dose of A to 2 doses of A per 1 dose of B, preferably from 2 doses of B per 1 dose of A to 3 doses of A per 2 doses of B. According to a preferred embodiment of the invention, the kit is designed to simultaneously release 1 dose by weight of A and 1 dose by weight of B.

According to the invention, the kit may be in any form that is compatible with, on the one hand, separate storage of the intermediate formulations A and B and, on the other hand, the ability to perform extemporaneous mixing of A and B.

For example, the intermediate formulations A and B may be packaged in a case with at least two separate compartments, each containing the formulations A or B.

According to another aspect, the kit may be in the form of a syringe having at least two separate bodies, each equipped with a piston, said two bodies containing the formulations A and B and being designed to simultaneously release, by exerting a force on the piston, the desired doses of the formulations A and B.

The invention also relates to a process for preparing a composition according to the invention, characterized in that, in order to obtain the composition in foam form, at least a dose of intermediate formulation A and a dose of intermediate formulation B of the kit as are defined above are mixed extemporaneously in relative weight proportions A/B that may range from 0.5 to 2, preferentially from 0.5 to 1.5 and more preferentially 1.

In order to obtain an optimum foam (final composition), the inventors experimentally sought the optimum contents of gas-generating agent (preferably sodium bicarbonate) and of gas-activating agent (preferably citric acid and/or disodium pyrophosphate and/or sodium dihydrogen phosphate).

Thus, it was determined experimentally that when the gas-activating agent is citric acid, the citric acid/sodium bicarbonate weight ratio in the total composition is between 0.1 and 2, preferentially between 0.5 and 1 and preferably equal to 0.7.

Similarly, it was determined that when the gas-activating agent is disodium pyrophosphate, the disodium pyrophosphate/sodium bicarbonate weight ratio in the total composition is between 0.5 and 5, preferentially between 1 and 3 and preferably equal to 2.4.

Similarly, it was determined that when the gas-activating agent is sodium dihydrogen phosphate, the sodium dihydrogen phosphate monohydrate/sodium bicarbonate weight ratio in the total composition is between 0.5 and 5, preferentially between 1 and 3 and preferably equal to 2.

The sodium bicarbonate/citric acid, sodium bicarbonate/sodium pyrophosphate and sodium bicarbonate/sodium hydrogen phosphate ratios are illustrated in example 4.

Surprisingly, the citric acid/sodium citrate, disodium pyrophosphate combination and a gelling system that is compatible with the galenical form made it possible to obtain a formulation with very stable physicochemical properties and in which clobetasol propionate is particularly stable and does not give rise to any unpleasant sensation on the skin and allows the release of gas and thus the creation of foam.

Example 2B below shows that the compositions according to the present invention have both excellent physical and chemical stability.

A composition is regarded as being physically stable when its organoleptic characteristics, its pH, its viscosity and the homogeneity of the clobetasol propionate do not change over time under various temperature conditions: room temperature (RT), 30° C. and 40° C.

According to the invention, room temperature corresponds to a temperature ranging from 15° C. to 25° C.

A composition is regarded as being chemically stable when the content of active principle it contains does not change over time under various temperature conditions (RT, 30° C. and 40° C.).

According to the invention, the composition is regarded as being stable when the content of active principle (expressed by weight relative to the weight of the intermediate formulation), measured by any known technique and in particular by HPLC, is included in the specifications ranging from 90% to 110%.

The composition according to the invention may also comprise one or more agents chosen from dispersants, solubilizers, stabilizers, preserving agents, fatty substances, thickeners, dyes, fragrances, surfactants, gelling agents, complexing agents, neutralizers, foaming emulsifying agents, non-foaming emulsifying agents, fillers, sequestrants, reducing agents, odor maskers, plasticizers, softeners, moisturizers, pigments, clays, mineral fillers, mineral colloids, polymers, proteins, nacreous agents, waxes, oils, for instance paraffins or silicones, fatty acids, solid esters of fatty alcohols or of fatty acids, gums and wetting agents.

Needless to say, a person skilled in the art will take care to select this or these optional additional adjuvants and/or the amount thereof such that the properties of the active agent(s) that may be added to the composition according to the invention are not, or are not substantially, adversely affected by the envisaged addition.

Water-soluble dyes, such as FD&C Blue 1 (of empirical formula $C_{37}H_{34}N_2Na_2O_9S_3$), and liposoluble dyes such as Sudan Red III or Nile Red have the advantage of coloring one of the formulation intermediates. This coloring makes it possible to monitor the satisfactory mixing of the two formulation intermediates and to highlight the formation of the foam.

Gelling Agents for the Intermediate Formulation Comprising the Gas Activator

The intermediate composition A preferably containing at least one gas-activating agent preferably contains at least one gelling agent and/or suspending agent.

Formulation A may contain large amounts of acid and of electrolytes.

As nonlimiting examples of gelling agents and/or suspending agents which are resistant simultaneously to electrolytes and to acidic pH values and which may be included in the compositions A according to the invention, mention may be made of ready-to-use mixtures, such as polyacrylate- 13 & polyisobutene & polysorbate 20 sold by SEPPIC under the name Sepiplus 400®, polysaccharides with, as nonlimiting examples, xanthan gum, such as Xantural 180® sold by the company Kelco, gellan gum sold under the name Kelcogel® by the company Kelco, *sclerotium* gum sold under the name Amigel® by Alban Muller Industrie, guar gum and derivatives thereof, such as the hydroxypropyl guar sold under the name Jaguar HP-105® by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M® Premium by the company Dow Chemical, or hydroxyethylcellulose, in particular the product sold under the name Natrosol HHX 250® by the company Aqualon, the family of the magnesium aluminum silicates, such as Veegum K®, Veegum Plus® or Veegum Ultra® sold by the company Vanderbilt, bentonite sold uner the name Polargel®HV, the family of modified starches, such as the modified potato starch sold under the name Structure Solanace®, the family of carrageenans, in particular divided into four main families: κ, λ, β and ω, such as the Viscarin® and Gelcarin® products sold by the company IMCD. Alternatively, polyvinyl alcohol, also known under the abbreviation PVA, sold by Merck under the name Polyvinyl Alcohol 40-88®. Preferably, Veegum K® and Xantural 180® will be used in combination.

The gelling agent as described above may be used at preferential concentrations ranging from 0.001% to 15% and more preferentially ranging from 0.15% to 5% by weight relative to the weight of the intermediate formulation A.

Gelling Agents for the Intermediate Formulation Containing the Gas Generator

The intermediate composition B preferably containing at least one gas-generating agent preferably contains at least one gelling agent and/or suspending agent.

As nonlimiting examples of gelling agents and/or suspending agents and/or gelling agents that are simultaneously resistant to electrolytes and two basic pH values and which may be included in the intermediate compositions B according to the invention, mention may be made of acrylic acid polymers such as the acrylates/C10-30 alkyl acrylate crosspolymer such as the "electrolyte-insensitive" carbomers sold under the name Ultrez 20®, Ultrez 10®, Carbopol 1382® or Carbopol ETD2020NF®, Aqua SF1® sold by the company Lubrizol, the ammonium acrylate/acrylamide copolymer & polyisobutene & polysorbate 20 mixture sold by SEPPIC under the name Sepiplus 265®, polysaccharides with, as nonlimiting examples, xanthan gum, such as Xantural 180® sold by the company Kelco, gellan gum sold under the name Kelcogel® by the company Kelco, *sclerotium* gum sold under the name Amigel® by Alban Muller Industrie, guar gum and derivatives thereof, such as the hydroxypropyl guar sold under the name Jaguar HP-105® or Jaguar S by Rhodia, cellulose and derivatives thereof, such as microcrystalline cellulose and sodium carboxymethyl cellulose sold under the name Blanose CMC 7H4XF® by the company Hercules, hydroxypropylmethylcellulose, in particular the product sold under the name Methocel E4M Premium® by the company Dow Chemical, or hydroxyethylcellulose, in particular the product sold under the name Natrosol HHX 250® by the company Aqualon, the family of the magnesium aluminum silicates, such as Veegum K®, Veegum Plus® or Veegum Ultra® sold by the company Vanderbilt, bentonite sold under the name Polargel®HV, the family of modified starches, such as the modified potato starch sold under the name Structure Solanace® or the tapioca meal known under the name Naviance Tapioca P® sold by AkzoNobel, or the family of carrageenans, in particular divided into four main families: κ, λ, β and ω, such as the Viscarin® and Gelcarin® products sold by the company IMCD.

The gelling agent as described above may be used at preferential concentrations ranging from 0.001% to 15% and more preferentially ranging from 0.15% to 5% by weight relative to the weight of the intermediate formulation B.

Humectants

Among the humectants and/or emollients which may act as skin moisturizer and facilitate the application of the formulation, use is optionally made, without this list being limiting, of compounds such as a polyol that is water-miscible at room temperature (25° C.) chosen especially from polyols especially containing from 2 to 20 carbon atoms, preferably containing from 2 to 10 carbon atoms and preferentially containing from 2 to 6 carbon atoms, such as glycerol, glycol derivatives such as propylene glycol, butylene glycol, pentylene glycol, hexylene glycol, dipropylene glycol or diethylene glycol, and mixtures thereof, but also sugars (for example glucose or lactose), polyethylene glycols (PEG) (for example Lutrol E400), urea, and amino acids (for example serine, citrulline, arginine, asparagine or alanine). As preferred humectant and/or emollient, mention may be made of glycerol and propylene glycol.

The humectants may be used, alone or in combination, at preferential concentrations ranging from 0.001% to 30% and more preferentially ranging from 0.01% to 10% by weight relative to the weight of the total formulation.

Solvent and Pro-Penetrating Agent

The composition according to the invention may comprise one or more solvents and/or pro-penetrating agents, which facilitate the penetration of the active principles and allow the dissolution of the active principle present in the composition according to the invention. More particularly, it is chosen from C1-C4 volatile alcohols, such as ethanol or isopropanol, or from glycol ethers, such as ethoxydiglycol sold by Gattefossé under the name Transcutol HP. It may be included in the formulation A in a content ranging from 0.1% to 10% and more preferentially between 0.5% and 2% by weight relative to the weight of the intermediate formulation A.

Chelating Agents

Among the chelating agents, mention may be made, as nonlimiting examples, of ethylenediaminetetraacetic acid (EDTA), diethylenetriaminepentaacetic acid (DTPA), ethylenediaminebis(O-hydroxyphenylacetic acid) (EDDHA), hydroxy-2-ethylenediaminetriacetic acid (HEDTA), ethyldiaminebis(O-hydroxy-p-methylphenyl)acetic acid (EDDHMA) and ethylenediaminebis(5-carboxy-2-hydroxyphenyl)acetic acid (EDDCHA).

As preferred chelating agent, mention may be made of ethylenediaminetetraacetic acid (EDTA) sold especially under the name Titriplex III®. It may be used at preferential concentrations ranging from 0.001% to 1% and more preferentially from 0.05% to 0.1% by weight relative to the weight of the total formulation.

Excipients with Specific Properties

The composition according to the invention may contain one or more cosmetic active agents, for instance, as nonlimiting examples, allantoin with anti-irritant properties, dipotassium glycyrrhizate for its anti-inflammatory properties, salicylic acid and coal tars with keratolytic properties, capsaicin which attenuates itching, or alternatively cicatrizing α-bisabolol or agents for conditioning the hair, such as polyquaterniums.

Fillers and Particles

Fillers and/or particles may be used to stabilize and boost the foam. Some of them have the specific property of being positioned at the water/air interface and of thus stabilizing this interface. Fillers that may be mentioned include talc, metal oxides such as zinc oxide, titanium dioxide TiO2 T2000 sold by the company Merck under the name Eusolex® T-2000, clays such as Laponites®, Bentones® or Bentonites®, but also cellulose ethers such as Methocel K100 LV® sold by the company Dow, silicas such as Aerosil® R972 sold by the company Evonik or Silice HDK® H13L sold by Wacker. They may be used at concentrations ranging from 0.01% to 10% by weight relative to the weight of the total formulation.

Preserving Agent:

Examples of preserving agents that may be mentioned include benzalkonium chloride, bronopol, chlorhexidine, chlorocresol and derivatives thereof, ethyl alcohol, phenoxyethanol, potassium sorbate, diazolidinyl urea, benzyl alcohol, parabens and sodium benzoate, or mixtures thereof.

As preferred preserving system, mention may be made of the combination of phenoxyethanol and pentylene glycol or sodium benzoate.

Foaming Surfactants of the Composition

The intermediate composition A may contain a small amount of foaming surfactants, which are advantageously compatible with clobetasol propionate.

As examples of surfactants that may be used, mention may be made of: anionic surfactants of the sulfonate family such as sodium C14-C16 olefin sulfonate, of the glycinate family such as sodium cocoyl glycinate sold by Clariant under the name Hostapon SG, of the isethionate family such as sodium cocoyl isethionate sold by Clariant under the name Hostapon SCI85 G, sodium lauroyl methyl isethionate sold by Innospec under the name Iselux LG, of the sulfate family such as zinc coceth sulfate sold by Zschimmer & Schwarz under the name Zetesol Zn or sodium laureth sulfate sold under the name Texapon N70, of the sulfosuccinate family such as disodium PEG-5 lauryl citrate sulfosuccinate sold by Evonik under the name Rewopol SB C55, disodium PEG-12 dimethicone sulfosuccinate sold by Rhodia under the name Mackanate Ultra Si, sodium cocoamphoacetate or disodium cocoamphodiacetate sold by Evonik under the name Rewoteric AMC and Rewoteric AM2CNM, sodium cocoyl glutamate sold under the name Protelan AGL95 by Zschimmer & Schwarz, sodium capryloyl glutamate sold under the name Protelan AG8 by Zschimmer & Schwarz or alternatively sodium lauroyl sarcosinate sold by Zschimmer & Schwarz under the name Protelan LS911.

Use may also be made of nonionic surfactants such as decylglucoside sold by Cognis under the name Plantacare 2000 UP, the glyceryl monolaurate sold by Rossow under the name Poem DL 100, or the sucrose laurate sold by Sisterna under the name Sisterna L70-C.

Use may also be made of amphoteric surfactants such as those of the betaine family such as the cocoyl betaine sold under the name Dehyton AB30 or the cocamidopropyl betaine sold under the name Tego Betaine F50.

These surfactants may be used alone or in combination. The total content of these surfactants is preferably less than or equal to 2.5% by weight, and more preferentially less than or equal to 1% by weight, relative to the weight of the total composition.

According to one embodiment, the composition according to the invention does not contain any foaming surfactant.

The examples that follow illustrate the invention without limiting its scope.

EXAMPLES

Example 1: Formulation Examples

Formulation Examples A: Intermediate Compositions Containing the Gas-Activating Agent, Formulated with an Acidic pH Intermediate formulations A were prepared according to the following process:

Step 1: At a temperature above 60° C., add the gelling agents and then the gas-generator activating agent(s) with stirring to the main water phase.

Step 2: In parallel, prepare the active phase by dissolving the clobetasol propionate in the solubilizing/pro-penetrating agent.

Step 3: At a temperature below 30° C., add the active phase to the main phase.

Step 4: Add the additives and the preserving agents, cosmetic active agents and chelating agents.

In the formulation examples below, the amounts are expressed relative to the weight of the intermediate formulation rather than relative to the weight of the total formulation.

Example A1

| INCI Name | % |
| --- | --- |
| WATER | QS 100 |
| DISODIUM EDTA | 0.1 |
| MAGNESIUM ALUMINIUM SILICATE | 2.5 |
| XANTHAN GUM | 0.7 |
| CITRIC ACID | 1.4 |
| SODIUM CITRATE | 1 |
| SODIUM PYROPHOSPHATE | 7.2 |
| SODIUM LAURETH SULFATE | 3.6 |
| COCO BETAINE | 1.3 |
| PROPYLENE GLYCOL | 4 |
| ETHOXYDIGLYCOL | 1.2 |
| CLOBETASOL PROPIONATE | 0.1 |
| SODIUM BENZOATE | 0.2 |

Example A2

| INCI Name | % |
| --- | --- |
| WATER | QS 100 |
| DISODIUM EDTA | 0.1 |
| MAGNESIUM ALUMINIUM SILICATE | 2.5 |
| XANTHAN GUM | 0.7 |
| CITRIC ACID | 3.5 |
| SODIUM CITRATE | 2.7 |
| SODIUM LAURETH SULFATE | 3.6 |
| COCO BETAINE | 1.3 |
| PROPYLENE GLYCOL | 4 |
| ETHOXYDIGLYCOL | 1.2 |

-continued

| INCI Name | % |
| --- | --- |
| CLOBETASOL PROPIONATE | 0.1 |
| SODIUM BENZOATE | 0.2 |

Example A3

| INCI Name | % |
| --- | --- |
| WATER | QS 100 |
| DISODIUM EDTA | 0.1 |
| MAGNESIUM ALUMINIUM SILICATE | 2.5 |
| XANTHAN GUM | 0.7 |
| CITRIC ACID | 3.5 |
| SODIUM CITRATE | 2.7 |
| PROPYLENE GLYCOL | 4 |
| ETHOXYDIGLYCOL | 3 |
| CLOBETASOL PROPIONATE | 0.1 |
| SODIUM BENZOATE | 0.2 |

Example A4

| INCI Name | % |
| --- | --- |
| WATER | QS 100 |
| DISODIUM EDTA | 0.1 |
| MAGNESIUM ALUMINIUM SILICATE | 2.5 |
| GUARD GUM | 0.4 |
| HYDROXYETHYL CELLULOSE | 0.5 |
| CITRIC ACID | 3.5 |
| SODIUM CITRATE | 2.7 |
| SODIUM LAURETH SULFATE | 3.6 |
| COCO BETAINE | 1.3 |
| PROPYLENE GLYCOL | 4 |
| ETHOXYDIGLYCOL | 1.2 |
| CLOBETASOL PROPIONATE | 0.1 |
| SODIUM BENZOATE | 0.2 |

Example A7

| INCI Name | % |
| --- | --- |
| WATER | QS 100 |
| DISODIUM EDTA | 0.1 |
| XANTHAN GUM | 0.7 |
| MAGNESIUM ALUMINIUM SILICATE | 2.5 |
| SODIUM BENZOATE | 0.2 |
| POLYVINYL ALCOHOL | 2 |
| DISODIUM PYROPHOSPHATE | 7.2 |
| PHENOXYETHANOL | 0.5 |
| CITRIC ACID | 1.4 |
| SODIUM CITRATE | 1 |
| POLOXAMER 124 | 0.2 |
| CLOBETASOL PROPIONATE | 0.1 |
| PROPYLENE GLYCOL | 4.0 |
| FD&C BLUE 1 | 0.0009 |

Formulation Examples B: Intermediate Compositions Containing the Gas-Generating Agent The intermediate formulations are formulated according to the following process:

Step 1': At a temperature above 60° C., add the gelling agents to the main water phase, with stirring.

Step 2': Add the cleansing agents or foaming agents and also the additives such as the preserving agents at a suitable temperature.

Step 3': Neutralize the mixture.

Step 4': At a temperature below 40° C., add sodium bicarbonate.

In a particular embodiment, a fatty phase (containing the oils, waxes and surfactants) may be heated to a temperature above 60° C. and incorporated into the main phase after step 1'.

Example B1

| INCI Name | % |
| --- | --- |
| WATER | QS100 |
| MAGNESIUM ALUMINIUM SILICATE | 2.5 |
| XANTHAN GUM | 0.5 |
| DISODIUM EDTA | 0.1 |
| DIPOTASSIUM GLYCYRRHIZATE | 0.5 |
| ZINC GLUCONATE | 0.4 |
| SODIUM C14-16 OLEFIN SULFONATE | 2 |
| SODIUM HYDROXIDE | 0.1 |
| SODIUM HYDROGEN CARBONATE | 5 |
| PHENOXYETHANOL | 1 |
| PENTYLENE GLYCOL | 5 |

Example B2

| INCI Name | % |
| --- | --- |
| WATER | QS100 |
| MAGNESIUM ALUMINIUM SILICATE | 2.5 |
| XANTHAN GUM | 0.6 |
| DISODIUM EDTA | 0.1 |
| SODIUM HYDROXIDE | 0.1 |
| SODIUM HYDROGEN CARBONATE | 3 |
| PHENOXYETHANOL | 1 |

Example B3

| INCI Name | % |
| --- | --- |
| WATER | QS100 |
| MAGNESIUM ALUMINIUM SILICATE | 2.5 |
| XANTHAN GUM | 0.5 |
| DISODIUM EDTA | 0.1 |
| DIPOTASSIUM GLYCYRRHIZATE | 0.5 |

-continued

| INCI Name | % |
|---|---|
| ZINC GLUCONATE | 0.4 |
| SODIUM C14-16 OLEFIN SULFONATE | 2 |
| SODIUM HYDROXIDE | 0.1 |
| SODIUM HYDROGEN CARBONATE | 3 |
| PHENOXYETHANOL | 1 |
| PENTYLENE GLYCOL | 5 |

The mixtures in a 1:1 weight ratio of the intermediate compositions A and B described above are represented in the table below. A cross at the intersection of two formulation intermediates indicates that the mixture was tested and generated a foam having the desired properties.

| | Formulation B | | |
|---|---|---|---|
| Formulation A | B1 | B2 | B3 |
| A1 | | X | |
| A2 | | X | |
| A3 | X | | X |
| A4 | | X | |
| A7 | X | | X |

Example 2A: Foam Density

From the formulation examples described in example 1, foam density measurements were taken at the moment of contact of the two intermediate formulations A and B (TO) and then when the chemical reaction generated by bringing the two compositions into contact is complete. These studies showed that the final composition is in the form of a foam with a suitable density.

Measurement of the foam density shows that the volume generated by one of the mixtures proposed in the above table has been increased by a factor of 3 to 5.

Example 2B: Stability

Table I below collates the physical stability data for the intermediate formulation A1 described in example 1, containing clobetasol propionate.

| Example A1 | T0 | | T 1 month | T 2 months | T 3 months |
|---|---|---|---|---|---|
| pH | 4.24 | 25° C. | 4.23 | 4.23 | 4.25 |
| | | 40° C. | 4.18 | 4.14 | 4.28 |
| Viscosity cP Brookfield RV DVII Spindle 5 speed 20 | 10160 | 25° C. | 12020 | 12530 | 10700 |
| | | 40° C. | 11450 | 10980 | 13000 |

Tables IIa and IIb below detail the chemical stability data for clobetasol propionate in the intermediate formulations A1 and A2 described in example 1.

| Example A1 | T0 | | T 1 month | T 2 months | T 3 months |
|---|---|---|---|---|---|
| W/W % clobetasol propionate (HPLC) | 101.4 | RT | 99.4 | 99.1 | 99.0 |
| | | 40° C. | 99.0 | 103.7 | 102.9 |

| Example A2 | T0 | | T 1 month | T 2 months | T 3 months |
|---|---|---|---|---|---|
| W/W % clobetasol propionate (HPLC) | 101.4 | RT | 99.5 | 99.6 | 100.4 |
| | | 40° C. | 99.9 | 99.7 | 99.7 |

Example 3: Comparative Study of Measurement of Irritation Study Protocol

The study is performed according to the OECD TG 439 protocol in force for the short application time (RHE/product contact time 15 min). This protocol is appropriate for a long application time (RHE/product contact time 18 h).

The objective of this study is to evaluate the tolerance of the supports of the complete and intermediate formulations on reconstructed human epidermides (RHE, Episkin model) through:
  evaluation of the reduction of MTT (cell viability)
  measurement of the release of IL-1alpha (irritation marker)

The formulations tested are:
  An intermediate composition of acidic formulation: example A7 placebo (i.e. not containing clobetasol propionate) and uncolored (i.e. not containing dyes),
  An intermediate composition of basic formulation: example B1
  The complete formulation 1 composed of the mixture: A7 placebo+B1 (in a 50/50 weight ratio)
  A commercial reference in the form of cleansing gel

| Mixture tested | Short exposure Viability (%) | Long exposure Viability (%) | Conclusion Irritant potential |
|---|---|---|---|
| B1 | 92.5 | 59.6 | Non-irritant |
| A7 placebo | 86.0 | 84.5 | Non-irritant |
| Whole formulation 1 | 93.2 | 86.8 | Non-irritant |
| Commercial ref. | 76.6 | 6.7 | Potentially irritant |

| Test item | Short exposure IL-1a vs control | Long exposure IL-1a vs control | Conclusion Irritant potential |
|---|---|---|---|
| B1 | 5.5 | 30.6 | Non-irritant |
| A7 placebo | 2.2 | 2.3 | Non-irritant |
| Whole formulation 1 | 4.5 | 11.6 | Non-irritant |
| Commercial ref. | 6.2 | 113.9 | Potentially irritant |

The MTT measurements according to the OECD protocol in force indicates that the rinse-out "whole formulation" tested is non-irritant whereas the "Commercial ref." is potentially irritant.

Furthermore, the assay of IL-la after application at long and short exposure times of the whole formulations shows a much lower level of irritation markers on the foam formulations than after application of the commercial reference.

Example 4

The ideal content of citric acid, sodium pyrophosphate and sodium dihydrogen phosphate monohydrate to react with 5% of sodium bicarbonate was established empirically. The values are expressed as weight/weight percentages relative to the weight of each of the two intermediate formulations

|  | Ratio 1 | Ratio 2 | Ratio 3 |
| --- | --- | --- | --- |
| Sodium bicarbonate | 5% | 5% | 5% |
| Citric acid | 3.5% | — | — |
| Disodium pyrophosphate | — | 12 | — |
| Sodium dihydrogen phosphate monohydrate | — | — | 7.2% |

In order for the pH of the formulation containing the gas activator to have optimum compatibility with the skin, sodium citrate was added so as to create a citric acid/sodium citrate buffer.

Part of the citric acid/sodium citrate buffer may advantageously be replaced with disodium pyrophosphate and vice versa following the contents cited by way of example in table I below:

TABLE III the values are expressed as weight/weight percentages relative to the weight of each of the two intermediate formulations.

|  | E 1 | E2 | E 3 | E 4 | E 5 | E 6 | E 7 |
| --- | --- | --- | --- | --- | --- | --- | --- |
| Sodium bicarbonate | 5% | 5% | 5% | 5% | 3% | 3% | 3% |
| Citric acid | 3.5% | 1.75% | 1.4% | 0 | 2.1% | 1.05% | 0 |
| Sodium citrate | 2.7% | 1.3% | 1% | 0 | 1.6% | 1.15% | 0 |
| Disodium pyrophosphate | 0 | 6% | 7.2% | 12% | 0 | 3.6% | 7.2% |

Part of the citric acid/sodium citrate buffer may advantageously be replaced with sodium dihydrogen phosphate monohydrate and vice versa, following the contents cited by way of example in table IV below:

TABLE IV

The values are expressed as weight/weight percentages relative to the weight of each of the two intermediate formulations.

|  | E1 | E8 | E9 |
| --- | --- | --- | --- |
| Sodium bicarbonate | 5% | 5% | 5% |
| Citric acid | 3.5% | 1.5% | 0 |
| Sodium citrate | 2.7% | 0.5% | 0 |
| Sodium dihydrogen phosphate monohydrate | 0 | 6.2% | 10% |

In one particular embodiment, it was determined that when the amount of citric acid is greater than or equal to 1.4, the amount of foam is optimal when disodium pyrophosphate is present in the composition according to the following equation:

$$[C] = 2.4[B] - 2.4[A]/0.7$$

when:
[C]=weight content of disodium pyrophosphate in the intermediate composition A
[A]=weight content of citric acid monohydrate in the intermediate composition A
[B]=weight content of sodium bicarbonate in the intermediate composition B The above equation thus makes it possible to calculate the optimum contents between sodium bicarbonate, citric acid and sodium pyrophosphate.

The invention claimed is:

1. A self-foaming rinse-off topical composition, comprising:
  (a) at least one intermediate composition B comprising (i) a gas-generating agent, and (ii) 0.5% to 5% by weight, relative to the weight of intermediate composition B, of one or more gelling agents and/or suspending agents selected from the group consisting of acrylic acid polymers, polysaccharides, cellulose and cellulose derivatives, magnesium aluminum silicates, modified starches, carrageenans, and combinations thereof;
  (b) at least one intermediate composition A comprising (i) an agent for activating the gas-generating agent, and (ii) 0.5% to 5% by weight, relative to the weight of intermediate composition A, of one or more gelling agents and/or suspending agents selected from the group consisting of mixtures of polyacrylate-13/polyisobutene/polysorbate 20, polysaccharides, cellulose and cellulose derivatives, magnesium aluminum silicates, modified starches, carrageenans, polyvinyl alcohol, and combinations thereof; and
  (c) 0.001% to 0.5% by weight, relative to the total weight of the composition, of clobetasol propionate, wherein the clobetasol propionate is present in intermediate composition A and/or B.

2. The composition as claimed in claim 1, wherein the clobetasol propionate is present in the intermediate composition A.

3. The composition as claimed in claim 1, wherein the composition comprises foaming surfactants at a concentration of less than or equal to 2.5% by weight, relative to the weight of the total composition.

4. The composition as claimed in claim 1, wherein the gas generated from the gas-generating agent is carbon dioxide.

5. The composition as claimed in claim 1, wherein the gas-generating agent is selected from the group consisting of sodium bicarbonate, potassium bicarbonate, sodium carbonate, potassium carbonate, and mixtures thereof.

6. The composition as claimed in claim 1, wherein the gas-generating agent is present in the intermediate composition B in an amount ranging from 1% to 10% by weight, relative to the weight of the intermediate composition B.

7. The composition as claimed in claim 1, wherein the intermediate composition B has a pH of from 7 to 12.

8. The composition as claimed in claim 1, wherein the agent for activating the gas-generating agent is selected from the group consisting of an acid, a partially salified polyacid salt, a buffer solution of a weak acid and of its conjugate base, and mixtures of these compounds.

9. The composition as claimed in claim 1, wherein the agent for activating the gas-generating agent is selected from the group consisting of citric acid, tartaric acid, malic acid, lactic acid, phosphoric acid, and pyrophosphoric acid, and the salts of these acids.

10. The composition as claimed in claim 1, wherein the agent for activating the gas-generating agent is a citric acid/sodium citrate buffer, alone or as a mixture with sodium phosphate and/or disodium pyrophosphate.

11. The composition as claimed in claim 1, wherein the agent for activating the gas-generating agent is present in the intermediate composition A in an amount ranging from 0.001% to 95% by weight relative to the weight of the intermediate composition A.

12. The composition as claimed in claim 1, wherein the intermediate composition A has an acidic pH.

13. The composition as claimed in claim 1, wherein the intermediate composition A is in the form of a solution, a gel or an emulsion.

14. The composition as claimed in claim 1, wherein the intermediate composition B is in the form of a solution, a gel or an emulsion.

15. A composition in foam form, wherein the composition is obtained by mixing of the intermediate compositions A and B as claimed in claim 1.

16. The composition as claimed in claim 1, wherein the composition further comprises one or more active agents selected from the group consisting of emollients, humectants, free-radical scavengers, anti-inflammatory agents, vitamins, depigmenting agents, antiacne agents, antiseborrheic agents, antifungal agents, keratolytic agents, sunscreens, slimming agents and skin-coloring agents.

17. The composition as claimed in claim 1, wherein the composition further comprises one or more agents selected from the group consisting of dispersants, solubilizers, stabilizers, preserving agents, fatty substances, thickeners, dyes, fragrances, surfactants, gelling agents, complexing agents, neutralizers, foaming emulsifying agents, non-foaming emulsifying agents, fillers, sequestrants, reducing agents, odor maskers, plasticizers, softeners, moisturizers, pigments, clays, mineral fillers, mineral colloids, polymers, proteins, nacreous agents, waxes, oils, for instance paraffins, silicones, fatty acids, solid esters of fatty alcohols or of fatty acids, gums and wetting agents.

18. A cosmetic method comprising topically applying an effective amount of the composition as claimed in claim 1 to the skin of an individual subject in need thereof, followed by removal of the composition by rinsing.

19. The composition as claimed in claim 1, wherein the composition is formulated for use in the treatment of psoriasis.

20. A kit or single multi-compartment container for a self-foaming topical composition, separately comprising at least two intermediate compositions:
(a) at least one intermediate composition B comprising (i) a gas-generating agent, and (ii) 0.5% to 5% by weight, relative to the weight of intermediate composition B, of one or more gelling agents and/or suspending agents selected from the group consisting of acrylic acid polymers, polysaccharides, cellulose and cellulose derivatives, magnesium aluminum silicates, modified starches, carrageenans, and combinations thereof;
(b) at least one intermediate composition A comprising (i) an agent for activating the gas-generating agent, and (ii) 0.5% to 5% by weight, relative to the weight of intermediate composition A, of one or more gelling agents and/or suspending agents selected from the group consisting of mixtures of polyacrylate-13/polyisobutene/polysorbate 20, polysaccharides, cellulose and cellulose derivatives, magnesium aluminum silicates, modified starches, carrageenans, polyvinyl alcohol, and combinations thereof; and
(c) 0.001% to 0.5% by weight, relative to the total weight of the composition, of clobetasol propionate, wherein the clobetasol propionate is present in intermediate composition A and/or B.

21. The kit or container as claimed in claim 20, wherein the kit or container is designed for mixing the intermediate compositions A and B in an A/B weight ratio ranging from 0.5 to 2.

22. A process for preparing a composition in foam form, the process comprising formulating the composition for rinse-off topical application, wherein the composition comprises clobetasol propionate, by mixing the intermediate composition A as defined in claim 1 with the intermediate composition B as defined in claim 1, in relative weight proportions A/B ranging from 0.5 to 2.

23. The composition as claimed in claim 3, wherein foaming surfactants are present and at a concentration of less than or equal to 1% by weight, relative to the total weight of the composition.

24. The composition as claimed in claim 5, wherein the gas-generating agent is sodium bicarbonate.

25. The composition as claimed in claim 6, wherein the gas-generating agent is present in the intermediate composition B in an amount ranging from 2% to 8% by weight, relative to the weight of intermediate composition B.

26. The composition as claimed in claim 7, wherein the pH is basic.

27. The composition as claimed in claim 9, wherein the agent for activating the gas-generating agent is selected from the group consisting of a citric acid/sodium citrate buffer alone, or phosphoric acid, sodium phosphate, and/or disodium pyrophosphate, which are alone or as a mixture with a citric acid/sodium citrate buffer.

28. The composition as claimed in claim 12, wherein the acidic pH is from 1 to 6.

29. The composition as claimed in claim 13, wherein the intermediate composition A is in the form of a gel.

30. The composition as claimed in claim 14, wherein the intermediate composition B is in the form of a gel.

31. The kit or container as claimed in claim 21, wherein the A/B weight ratio is from 0.5 to 1.5.

32. The kit or container as claimed in claim 21, wherein the A/B weight ratio is from 0.9 to 1.1.

33. The kit or container as claimed in claim 21, wherein the A/B weight ratio is 1.

34. The process as claimed in claim 22, wherein the A/B weight proportion ranges from 0.5 to 1.5.

35. The process as claimed in claim 22, wherein the A/B weight proportion is 1.

36. The composition as claimed in claim 1, wherein the composition does not comprise any foaming surfactants.

* * * * *